(12) United States Patent
Sugai et al.

(10) Patent No.: US 7,776,325 B2
(45) Date of Patent: Aug. 17, 2010

(54) **BACTERICIDE AGAINST *STREPTOCOCCUS MUTANS* AND *STREPTOCOCCUS SOBRINUS***

(75) Inventors: Motoyuki Sugai, Hiroshima (JP); Hitoshi Komatsuzawa, Hiroshima (JP)

(73) Assignee: Two Cells Co., Ltd., Hiroshima (JP)

( * ) Notice: Subject to any disclaimer, the term of this patent is extended or adjusted under 35 U.S.C. 154(b) by 1070 days.

(21) Appl. No.: 10/583,127

(22) PCT Filed: Nov. 29, 2004

(86) PCT No.: PCT/JP2004/017682

§ 371 (c)(1), (2), (4) Date: Jun. 16, 2006

(87) PCT Pub. No.: WO2005/058343

PCT Pub. Date: Jun. 30, 2005

(65) Prior Publication Data

US 2008/0311056 A1 Dec. 18, 2008

(30) Foreign Application Priority Data

Dec. 17, 2003 (JP) .............................. 2003-419123

(51) Int. Cl.
*A61K 38/43* (2006.01)
(52) U.S. Cl. .................................................. 424/94.1
(58) Field of Classification Search ........................ None
See application file for complete search history.

(56) References Cited

U.S. PATENT DOCUMENTS

2003/0129146 A1  7/2003  Fischetti et al.

FOREIGN PATENT DOCUMENTS

| JP | 10/136976 | 5/1998 |
| JP | 2002-114709 | 4/2002 |
| WO | WO02/077183 | 10/2002 |

OTHER PUBLICATIONS

Baba et al. (Jpn. J. Oral. Biol., 25:947-955, 1983).*
Ajdić, D. et al., Genome Sequence of *Streptococcus mutans* UA159, a cariogenic dental pathogen. *PNAS.* vol. 99, No. 22 pp. 14434-14439 (2002).
Kim et al., Purification and Properties of Bacteriolytic Enzymes from *Bacillus licheniformis* YS-1005 against *Streptococcus mutans. Bioscience, Biotechnology, and Biochemistry.* vol. 63, No. 1 pp. 73-77 (1999).
Shibata et al., Identification and Characterization of an Autolysin-Encoding Gene of *Steptococcus mutans. Infection and Immunity.* vol. 73, No. 6 pp. 3512-3520 (2005).
Supplementary European Search Report corresponding to International Patent Application No. 04820505.8-2403/1716862 dated Jun. 12, 2009.
Yoshimura et al., Identification and Molecular Characterization of an N-Acetylmuraminidase, Aml, Involved in *Streptococcus mutans* Cell Separation. *Microbiology Immunology.* vol. 50, No. 9 pp. 729-742 (2006).
Yoshimura et al., Zymographic Characterization of Bacteriolytic Enzymes Produced by Oral Streptococci. *Microbiology Immunology.* vol. 48, No. 6 pp. 465-469 (2004).
Shibata et al., *Cloning of autolytic enzyme gene in carious bacteria.* Presentation at Japanese Association for Oral Biology 45th annual meeting on Sep. 1, 2003.
Yoshimura et al., *Hydrolase of peptidoglycan produced by streptococci in oral cavity.* Presentation at Japan Society for Bacteriology No. 75 plenary session on Apr. 4-6, 2002.
Abstract only, Baba et al., Studies on the lytic enzyme from *Streptococcus mutans. Japanese Journal of Oral Biology.* vol. 26 pp. 185-194 (1984).
Abstract only, Hamada, Shigeyuki, Characterization of Virulence Factors of Mutans Streptococci and Specific Inhibition of These Factors. *Journal of Japanese Society for Bacteriology.* vol. 51, No. 4 pp. 931-951 (1996).
Abstract only, Nosaki, Yoshihiro, Lysis of Oral Streptococci by an Extracellular Enzyme from the Bacterium *Streptococcus mutans. Kanagawa Odontology.* vol. 24, No. 2 pp. 384-392 (1989).
Abstract only, Sugai et al., Bacteriolytic Enzymes Produced by the Staphylococci. *Japanese Journal of Bacteriology.* vol. 52, No. 2 pp. 461-473 (1997).

* cited by examiner

*Primary Examiner*—Robert B Mondesi
*Assistant Examiner*—Brian J Gangle
(74) *Attorney, Agent, or Firm*—Jenkins, Wilson, Taylor & Hunt, P.A.

(57) ABSTRACT

The present invention provides an enzyme with lytic activity against cariogenic bacteria and a means for treating and preventing tooth decay using the enzyme. The enzyme provided by the present invention is a lytic enzyme produced by *Streptococcus mutans* and has a substrate specificity for lysing selectively *Streptococcus mutans* and *Streptococcus sobrinus*. Therefore, application of the enzyme enables to remove selectively cariogenic bacteria or to decrease the number of cariogenic bacteria inside oral cavity, and may exert preventive effect against tooth caries.

4 Claims, 5 Drawing Sheets

SEQUENCE LISTING

```
<160> NUMBER OF SEQ ID NOS: 4

<210> SEQ ID NO 1
<211> LENGTH: 979
<212> TYPE: PRT
<213> ORGANISM: Streptococcus mutans

<400> SEQUENCE: 1

Met Lys Ser Lys Thr Tyr Leu Met Ile Pro Leu Ala Leu Thr Leu Phe
1               5                   10                  15
```

-continued

```
Met Ala Ala Asn Lys Ile Ser Ala Asp Glu Gln Asn Gln Ser Leu Ser
             20                  25                  30

Ala Ser Glu Val Ile Ser Ser Asp Ala Thr Ser Val Ser Glu Leu Pro
         35                  40                  45

Ala Thr Thr Ala Gln Ile Ser Gln Glu Val Arg Asn Asn Gly Gln Asp
     50                  55                  60

Ser Thr Ile Gln Leu Gln Gln Thr Gln Glu Gln Ser Asp Pro Ile Thr
 65                  70                  75                  80

Ser Thr Ser Glu Thr Thr Val Ser Ser Met Lys Ala Val Thr Asn Gly
                 85                  90                  95

Ser Pro Ala Lys Ala Asn Glu Thr Glu Thr Val Pro Ser Gln Ala Ser
            100                 105                 110

Thr Ala Ser Ser Val Gln Thr Pro Asp Gln Ile Ser Thr Val Pro Ser
        115                 120                 125

Val Lys Ala Glu Thr Thr Ser Thr Ala Asp Gln Leu Gln Ser Thr Ser
    130                 135                 140

Ser Ala Pro Leu Asp Gln Gln Thr Asp Ala Lys Arg Leu Ser Asn Lys
145                 150                 155                 160

Met Thr Pro Ala Ser Ser Val Gln Ala Arg Ser Ser Leu Thr Gln Asp
                165                 170                 175

Lys Gln Val Gln Ala Gln Glu Val Thr Ser Ala Val Val Glu Glu Lys
            180                 185                 190

Gly Ile Lys Leu Gln Tyr Asn Gly Gln Ile Ala Arg Asn Thr Lys Ile
        195                 200                 205

Gln Phe Ala Val Trp Ser Ala Arg Asn Asp Gln Asp Asp Leu Gln Trp
    210                 215                 220

Tyr Thr Ala Asn Asn Met Gly Ala Ala Tyr Ala Glu Phe Lys Asn His
225                 230                 235                 240

Arg Glu Tyr Gly Thr Tyr Tyr Val His Thr Tyr Ala Asn Gln Asn Gly
                245                 250                 255

Lys Met Ile Gly Leu Asn Ala Thr Thr Leu Thr Ile Ala Gln Pro Gln
            260                 265                 270

Val Gln Thr Asn Ile Gln Arg Lys Ser Ala Thr Asn Phe Glu Leu Thr
        275                 280                 285

Val Ser Asn Val Pro Asn Thr Ile Ser Ser Ile Met Val Pro Val Trp
    290                 295                 300

Ser Asp Gln Asn Gly Gln Asp Ile Lys Trp Tyr Asn Ala Arg Lys
305                 310                 315                 320

Ala Asp Asp Gly Ser Tyr Lys Ala Leu Ile Asp Thr Lys Asn His Lys
                325                 330                 335

Asn Asp Leu Gly His Tyr Glu Ala His Ile Tyr Gly Tyr Ser Thr Val
            340                 345                 350

Thr Gln Ser Gln Ile Gly Leu Ala Val Ser Ser Gly Phe Asp Arg Asn
        355                 360                 365

Asp Thr Arg Pro Asn Ala Arg Ile Ser Val Ala Asp Tyr Asp Gln Asn
    370                 375                 380

Lys Thr Thr Phe Asp Val Val Glu Gly Ser Ser Asp Thr Lys Thr
385                 390                 395                 400

Val Ser Ala Val Asn Ile Ala Val Trp Ser Glu Asp Lys Gly Gln Asp
                405                 410                 415

Asp Leu Lys Trp Tyr Ser Pro Lys Ile Val Asn Asn Lys Ala Thr Val
            420                 425                 430
```

-continued

```
Thr Ile Asn Ile Ala Asn His Ser Asn Thr Ser Asp Lys Tyr Asn Val
            435                 440                 445

His Val Tyr Thr Asp Tyr Thr Asp Gly Thr His Ser Gly Thr Ile Leu
    450                 455                 460

Gly Ala Tyr Gln Ile Asn Lys Pro Leu Glu Lys Asn Thr Val Ser Ala
465                 470                 475                 480

Asp Leu Thr Ser Asp Gly Ile Ala Leu Lys Leu Asp Ser Asn Thr Val
                485                 490                 495

Thr Asp Tyr Thr Lys Val Arg Phe Ala Val Trp Ser Asp Gln Asn Gly
            500                 505                 510

Gln Asp Asp Leu Lys Trp Tyr Ser Ala Asn Ser Asp Gly Ala Ala Thr
        515                 520                 525

Ala Ala Tyr Ser Asn His Ser Gly Tyr Gly Leu Tyr His Ile His Thr
    530                 535                 540

Tyr Ile Ile Lys Asp Gly Glu Met Val Gly Leu Asn Gly Arg Thr Ile
545                 550                 555                 560

Thr Ile Asn Gln Pro Ser Ala Lys Val Asp Ile Ala Lys Glu Ser Asp
                565                 570                 575

Ala Leu Tyr Lys Val Thr Val Ser Asn Leu Pro Ala Tyr Ile Ser Ser
            580                 585                 590

Val Ala Ile Pro Val Trp Thr Asp Lys Asn Asn Gln Asp Asp Ile Gln
        595                 600                 605

Trp Ile Leu Ala Thr Lys Gln Gly Asp Gly Thr Tyr Ala Ala Gln Ile
    610                 615                 620

Gln Leu Ala Asp His Asn Gly Glu Thr Gly His Tyr Asn Val His Val
625                 630                 635                 640

Tyr Gly Gln Ser Lys Phe Asp Asn Lys Thr Val Gly Leu Ala Ala Thr
                645                 650                 655

Asp Gly Phe Asn Val Ala Glu Thr Arg Asn Ala Val Ile Ala Ala Ser
            660                 665                 670

Asn Tyr Asn Ala Ser Ala Gly Thr Ile Asp Met Ile Val Lys Gln Glu
        675                 680                 685

Ala Gly Gly Lys Ala Ile Lys Glu Val Arg Ile Ala Ala Trp Ser Glu
    690                 695                 700

Ala Asp Gln Ser Asn Leu His Trp Tyr Val Ser Ser Thr Ile Ile Asp
705                 710                 715                 720

Gly Lys Val Thr Val Thr Ile Asn Glu Lys Asn His Gln Tyr Ile Lys
                725                 730                 735

Gly Asn Tyr Asn Ile His Val Tyr Val Asp Tyr Thr Asp Gly Thr Ser
            740                 745                 750

Ser Gly Thr Asn Ile Gly Asn Tyr Ser Leu Asn Ala Asp Lys Pro Ala
        755                 760                 765

Val Ala Leu Pro Ser Tyr Phe Ile Asp Ile Ser Ser His Asn Gly Ile
    770                 775                 780

Ile Ser Val Ala Glu Phe Asn Ser Leu Lys Gln Gln Gly Ile Gln Gly
785                 790                 795                 800

Val Val Val Lys Leu Thr Glu Gly Thr Ser Tyr Ile Asn Pro Tyr Ala
                805                 810                 815

Ser Ser Gln Ile Ala Asn Ala Arg Ala Ala Gly Ile Lys Val Ser Ala
            820                 825                 830

Tyr His Tyr Ala His Tyr Thr Ser Ala Ala Gly Ala Gln Glu Glu Ala
        835                 840                 845

Arg Tyr Phe Ala Asn Ala Ala Arg Ser Phe Gly Leu Glu Ala Ser Thr
```

```
                850              855              860
Val Met Val Asn Asp Met Glu Glu Ser Ser Met Val Asn Asn Ile Asn
865                      870                      875              880

Asn Asn Val Gln Ala Trp Gln Asp Glu Met Arg Arg Gln Gly Tyr Ser
                885                      890                      895

Asn Leu Ile His Tyr Thr Met Ala Ser Trp Leu Asp Ile Arg Gly Gly
                900                      905                      910

Gln Val Asp Thr Ala Arg Phe Gly Ile Asn Asn Phe Trp Val Ala His
                915                      920                      925

Tyr Ala Lys Gly Tyr Thr Tyr Met Thr Gln Glu Ala Lys Ser Leu
            930                      935                      940

Asn Tyr Tyr Ala Asn Ala Ala Ala Trp Gln Tyr Thr Ser Val Ser Ser
945                      950                      955                      960

Lys Leu Ser His Ala Leu Asp Glu Asn Ile Asp Tyr Thr Gly Arg Phe
                    965                      970                      975

Thr Gln Gln
```

<210> SEQ ID NO 2
<211> LENGTH: 2940
<212> TYPE: DNA
<213> ORGANISM: Streptococcus mutans

<400> SEQUENCE: 2

```
atgaaaagca aaacttattt gatgattcca ttagcattga ccctatttat ggctgctaat     60
aaaatatctg cagatgagca aaatcaatcc ttaagtgcat cagaagttat ttcttctgat    120
gcgacatcag tatctgaatt accagcgaca acagcacaga taagtcagga agtcagaaat    180
aatggacaag acagtactat tcaattgcag caaacacagg aacagtctga tccgataaca    240
agtacgtctg agacaactgt ttcctctatg aaggcggtca caaatggctc acctgccaaa    300
gcaaatgaga ctgaaacagt tccgtctcag gcaagtactg ctagttctgt gcagactcct    360
gatcagattt cgactgttcc ctctgtaaaa gcagaaacca cttctaccgc agatcaatta    420
caatcaacat catctgctcc tttggatcaa caaactgatg ctaaacgtct ttccaataaa    480
atgactccag caagcagcgt acaagctcgt tcttctctta cacaagacaa gcaagtacag    540
gcacaggaag tcacaagtgc tgtagtggaa gaaaaaggga ttaagctaca gtataacggt    600
cagatcgctc gaaatactaa gattcaattt gctgtctggt cagctcgaaa tgatcaagat    660
gatcttcaat ggtatacggc aaataatatg ggagcggcct atgctgaatt caagaatcat    720
cgtgagtatg ggacctatta tgttcatact tatgctaatc aaaatggcaa gatgatagga    780
cttaacgcaa caactcttac aattgctcaa cctcaggtgc aaactaatat tcaaagaaaa    840
tcagcaacga attttgagtt aaccgtttct aatgttccta atactattag cagcatcatg    900
gtacctgtct ggtcagatca aaacggtcaa gatgatatta atggtataa tgcccgaaag    960
gctgatgatg gcagttataa ggctttgatt gatactaaaa atcacaagaa tgatttggga   1020
cattatgaag ctcatatttta cggctacagc acagtaaccc agtctcaaat tggcttagct   1080
gttagttctg gttttgaccg caatgatact agacccaatg caaggatatc tgttgctgat   1140
tatgaccaaa ataaaacgac ctttgatgtt gttgttgagg ttcatctgaa tacaaagact   1200
gtatctgctg ttaatattgc tgtttggtct gaagataaag gtcaagatga ccttaagtgg   1260
tattcaccaa aaattgtcaa caataaggca actgtgacga ttaatatcgc taatcattca   1320
aatacttcag ataaatataa tgtccatgtt tatacagact acactgatgg gacacattct   1380
```

-continued

```
ggtactattt tagggcttta tcagatcaat aaaccgcttg agaaaaatac tgtttcagct    1440
gatttaacta gtgatggcat tgctctcaaa ttagattcaa acacggttac agattatacc    1500
aaagtacgat ttgccgtttg gtcggatcaa aatggtcaag atgatctcaa gtggtatagt    1560
gcaaatagtg atggagcggc aactgcagct tacagtaacc acagtggtta tgggctttat    1620
catatccata cttatattat taaagatggg gaaatggttg ggcttaatgg cagaacgata    1680
actattaatc agcctagtgc caaggttgat attgctaaag aatccgatgc tctttataaa    1740
gtgactgttt ctaacctgcc agcttacatt agttcagtag ctattcctgt ctggacagat    1800
aaaaacaatc aagatgatat tcaatggatt ctcgcgacaa acaaggtga tggaacctac     1860 gcagcgcaaa ttcagttagc tgatcataat ggggaaacag gccattataa tgttcatgtc    1920
tatgacaaaa gtaaatttga caataaaacg gttggcttag cagcaactga tggctttaat    1980
gttgcagaga caaggaatgc tgttatcgct gcttcaaatt ataatgccag tgcaggaacg    2040
atagatatga ttgttaaaca agaagcgggt ggtaaagcga tcaaagaagt tcggatagct    2100
gcttggtcag aagctgatca atctaacctt cattggtatg tttcatcaac tattattgat    2160
ggtaaggtaa cagtcaccat taatgaaaaa aatcatcaat atattaaagg aaattataac    2220
attcatgtct atgttgatta tactgatggc actagtagcg gaaccaatat tggaaactat    2280
agcttgaatg ctgataaacc tgctgttgct ctgccatctt actttattga tattagtagc    2340
cacaatggaa tcatttctgt tgccgaattc aatagcttga acaacaagg tattcaagga    2400 gtggttgtta agttaacaga aggtacaagc tacatcaatc cttatgcaag ttctcaaatt    2460
gccaatgcca gagctgccgg tattaaggtt tctgcttacc actatgctca ctatacttct    2520
gcggctgggg cacaagaaga agcccgttat tttgctaatg cagccagatc ctttggtttg    2580
gaggcatcaa ctgtcatggt caatgatatg gaagagtcct ctatggtgaa caatattaat    2640
aataatgttc aagcttggca agatgagatg aggcgtcaag gttatagcaa cctgattcat    2700
tatactatgg ctagttggtt ggatatacgc ggtgggcaag tagacactgc aaggtttggc    2760
atcaataatt tttgggttgc tcattatgcc aaagggtata cttatatgac tcaagaagaa    2820
gctaaatccc ttaattatta tgctaatgca gcagcttggc agtatactag tgtatcgtct    2880
aaattgtctc atgctttgga tgaaaatatt gattatactg gtcgatttac tcaacagtaa    2940
```

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
agttcctgcc atactactgt                                                20

<210> SEQ ID NO 4
<211> LENGTH: 28
<212> TYPE: DNA
<213> ORGANISM: artificial sequence
<220> FEATURE:
<223> OTHER INFORMATION: primer

<400> SEQUENCE: 4
caggatccgt acaagctcgt tcttctct                                       28

BACTERICIDE AGAINST *STREPTOCOCCUS MUTANS* AND *STREPTOCOCCUS SOBRINUS*

CROSS REFERENCE TO RELATED APPLICATIONS

This application is a National Stage of International Application No. PCT/JP2004/017682, filed Nov. 29, 2004, which claims the benefit of Japanese Patent Application No. 2003-419123, filed on Dec. 17, 2003, and are incorporated by reference herein in their entirety.

FIELD OF THE INVENTION

The present invention relates to an enzyme having a bacteriolytic activity against *Streptococcus mutans* and *Streptococcus sobrinus*, and a means for protecting and treating tooth decay using the enzyme, and more particularly to toothpaste, gum and the like using the enzyme having a purpose of protection and treatment of tooth decay.

PRIOR ART

It has been elucidated based on numerous experimental studies using germfree rats and epidemiological studies that cariogenic bacteria inducing human tooth caries are *Streptococcus mutans* and *Streptococcus sobrinus* belonging to the group of streptococci (reference 3). During the study of bacteriolytic enzyme, which decomposes metabolically a big construct, peptidoglycan, contained in bacteria, the present inventors are interested in and are studying bacteriolytic enzyme produced by *Streptococcus mutans* (reference 4). Peptidoglycan is a construct involved in only eubacteria and archaebacteria among various living organisms, which has a mesh wire structure textured with sugar and peptide chains, and enwraps a bacterial cell. The structure of peptidoglycan is comparable to a bone structure maintaining a bacterial shape in order to hold the inner pressure with about 20 atms. Peptidoglycans have been considered as a target of antibacterial chemotherapeutic agents for a long time because of their specificities. A lot of antibiotic therapeutic agents, including β-lactam antibiotics such as penicillin G making a dent of antibiotics, are agents with their targets on biosynthesis of peptidoglycan systems. β-lactam medications have excellent selective toxicity because of lack of targets on animal cells and have been widely used as medical agents with minimal side effects.

On the other side, Hisae Baba et al. reported an enzyme, AL-7, with similar characteristics to the enzyme of the present invention produced by *S. mutans* (reference 5-7) and elucidated that the enzyme, AL-7, lyses selectively heated bacterial bodies of *Streptococcus sanguis* and *Streptococcus mutans*.

In addition to the above example, some examples concerning the enzymes produced by *S. mutans* have been reported (references 1~2 and others).

Reference 1: Japan Patent JP H10-136976
Reference 2: Japan Patent JP 2002-114709
Reference 3: Journal of Japanese Soc. for Bacteriology 51(4): 931-951, (1996)
Reference 4: ibid. 52(2): 461-473, (1997)
Reference 5: J. Oral Biol., 25:947-955, 1983
Reference 6: J. Oral Biol., 26:185-194, 1984
Reference 7: Kanagawa Odontology, 24-2, 384-392, 1989

Problems to be Solved by the Invention

Previously, it has been generally accepted as a concept of antibacterial chemotherapy that medical agents have targets common to various bacteria and that preferred action affects lethally to the targets. However, the action affects not only to bacteria targeted by chemotherapy but also to bacterial group forming normal bacterial flora, and induces replacement of bacteria. Furthermore, once bacteria acquire resistance to medical agents, rapid spreading of the resistance beyond a barrier of bacterial species will be recognized. Therefore, antibacterial chemotherapeutic agents, different from previous antibacterial agents, has been sought, which is effective to specific cariogenic bacteria.

Namely, the purpose of the present invention is to provide an enzyme attacking selectively cariogenic bacteria and a means for preventing and treating tooth decay using the enzyme.

Means to Solve the Problems

Bacteriolytic enzyme is an enzyme essential for metabolyzing peptidoglycans during growth phase, wherein bacteria undergo mitosis and cell segregation. The present inventors discovered bacteriolytic enzyme Lyt100 produced by *Streptococcus mutans* during investigations, cloned the gene, constructed recombinants and examined the function of the enzyme. During the examination of the substrate specificity of the enzyme, the inventors discovered that the enzyme has a substrate specificity to lyse selectively *Streptococcus mutans* and *Streptococcus sobrinus*. The enzyme, which lyses selectively *Streptococcus mutans* and *Streptococcus sobrinus*, has advantages in lysing the cariogenic bacteria without affecting normal bacterial flora existing in mouth. Use of the enzyme enables to remove selectively cariogenic bacteria or to decrease the number of cariogenic bacteria inside oral cavity, and may exert preventive effect against tooth caries.

Namely, the present invention is a bactericide against *Streptococcus mutans* and *Streptococcus sobrinus* comprising any one of the following proteins (1) to (3):

(1) a protein shown by the amino acid sequence of SEQ ID NO: 1 or a protein having the amino acid sequence derived therefrom in which one or more amino acids (for example, maximum 5% of total amino acids.) are deleted, substituted of added and having a lytic activity against *Streptococcus mutans* or *Streptococcus sobrinus*.

(2) a protein having a 100±10 kDa band of lysed bacteria in a zymography containing killed *Streptococcus mutans*.

(3) a protein obtained from cultured cells transformed by DNA comprising nucleotide sequence of SEQ ID NO: 2 or DNA encoding said protein (1)

Furthermore, the present invention is a preventive agent of tooth decay, a therapeutic agent of tooth decay, a toothpaste, an oral cavity cleaner or a preventive gum of tooth decay, containing the bactericide. Prescription of the above agents are according to conventional means of various fields.

Moreover, the present invention is a method for killing selectively *Streptococcus mutans* and *Streptococcus sobrinus* using any one of the following proteins (1) to (3):

(1) a protein shown by the amino acid sequence of SEQ ID NO: 1 or a protein having the amino acid sequence derived therefrom in which one or more amino acids are deleted, substituted of added and having a lytic activity against *Streptococcus mutans* or *Streptococcus sobrinus*.

(2) a protein having a 100±10 kDa band of lysed bacteria in a zymography containing killed *Streptococcus mutans*.

(3) a protein obtained from cultured cells transformed by DNA comprising nucleotide sequence of SEQ ID NO: 2 or DNA encoding said protein (1).

DETAILED DESCRIPTION OF THE INVENTION

Figure 1:
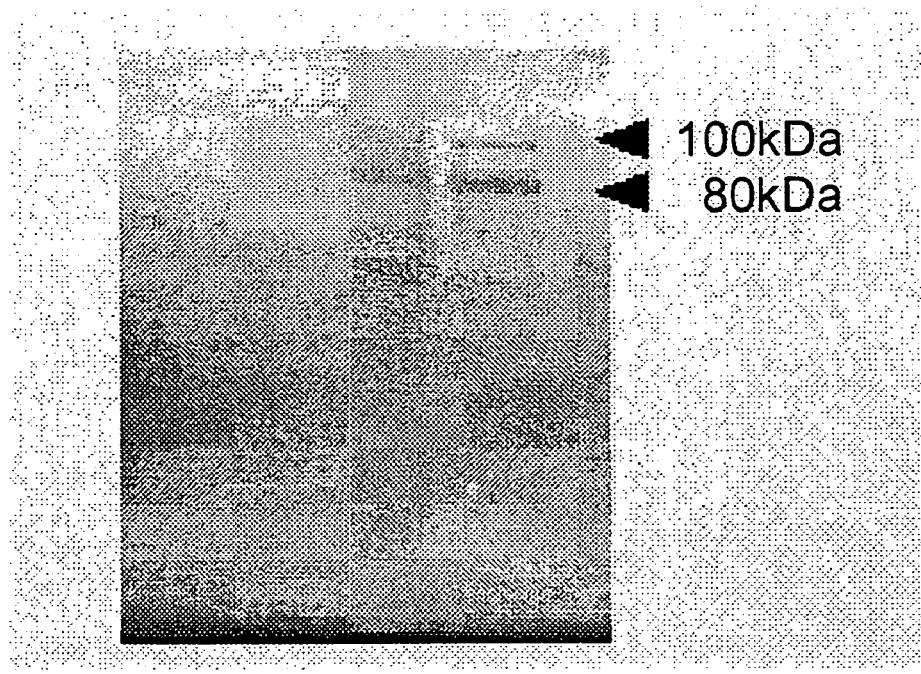
FIG. 1 is the zymogram of the enzyme Lyt100 of the present invention

The enzyme Lyt100 of the present invention is different from the enzyme AL-7 produced by *Streptococcus mutans*. (reference 5), although AL-7 has a similar characteristics to Lyt100 of the present invention. First of all, AL-7 is an extracellular enzyme, while Lyt100 is an intracellular enzyme. 20 mg AL-7 enzyme sample shows maximum 17% and 20.6% lytic activity against heat killed *Streptococcus mutans* and *Streptococcus obrinus*, respectively; and shows 6% and 8.3% lysing activity against cell wall of *Streptococcus mutans* and *Streptococcus sobrinus*, respectively. On the other hand, by using the similar assay system, 3 µg Lyt100 enzyme shows maximum 23% and 33.6% lytic activity against heat killed *Streptococcus mutans* and *Streptococcus sobrinus*, respectively; and shows 96.7% and 96.7% lysing activity against cell wall of *Streptococcus mutans* and *Streptococcus obrinus*, respectively. Lyt100 has a stronger lysing activity against cell wall than AL-7. Whereas, for viable cells, 20 mg AL-7 enzyme shows maximum 3.2% and 3.3% lytic activity against *Streptococcus mutans* and *Streptococcus sanguis*, respectively, i.e. AL-7 enzyme has almost no lytic activity against viable cells and has no species specificity. On the contrary, 10 µg Lyt100 enzyme shows 44% and 56% lytic activity against *Streptococcus mutans* and *Streptococcus sobrinus*, respectively, and 0% lytic activity against *Streptococcus sanguis*. *Streptococcus salivarius* and *Streptococcus mitis*, i.e. Lyt100 enzyme has a strong lytic activity with species specificity against *Streptococcus mutans* and *Streptococcus sobrinus*.

Lyt100 enzyme of the present invention is an enzyme produced in a pathogenic bacteria (*Streptococcus mutans*) and lyses and kills the same pathogenic bacteria themselves. Since the enzyme has strong species specificity and does not affect to other bacterial flora, it can be applied for treatment and protection of decayed tooth.

The following examples illustrate the present invention more clearly, but it is not intended to limit the scope of the present invention.

Example 1

(1) Preparation of Crude Enzyme

After *Streptococcus mutans* strain MT703R (hereinafter, *S. mutans*) was cultured in 600 ml brain-heart-infusion medium at 37° C. overnight, cells were centrifuged at 8000×g for 20 min and a pellet (about 1.2 g) was obtained. The pellet was added 2 ml of 8 M urea, was suspended and was left to stand at room temperature for 30 min. The suspension was centrifuged at 15,000×g for 15 min and the supernatant was obtained. The supernatant was concentrated in a membrane ultrafilter (Amicon). The final concentration was adjusted to 1 mg/ml and it was used as crude enzyme.

(2) Discovery of Lytic Enzyme Lyt100

The crude enzyme was applied to a zymography. A zymography is a method of applying SDS polyacrylamide gel electrophoresis for assaying a lytic enzyme activity. Firstly, killed cells (1 mg/ml) of *S. mutans* were added to polyacrylamide gel at the time of gel polymerisation. Then, after usual electrophoresis, the gel was washed with water, was incubated in 0.1 M phosphate buffer (pH 7.0) to recover the lytic enzyme activity inside the gel. The recovered lytic enzyme lyses the killed cells near the protein band and leads to be detected as a transparent band with a background of white turbid gel. The obtained gel is referred to as zymogram.

The killed cells of *S. mutans* was used after treatment of cells with 100° C. hot water/4% SDS for 30 to 60 min and subsequently after washing with enough volume of PBS for ten times.

As shown in FIG. 1, two lytic bands were observed in the region of high molecular weight. After the SDS gel electrophoresis of the crude enzyme, the protein in the gel was stained with Coomassie brilliant blue and the protein bands corresponding to the lytic band were checked by comparing to the zymogram. The two protein bands contained in the gels (corresponding to two lytic activities) were cut out, were transferred to a Nylon (R) membrane and were applied to gas phase amino acids sequence analyzer (Model 49X Precise). Based on the obtained amino acids sequence (SEQ ID NO: 1), DNA fragment comprising the nucleotide sequence (SEQ ID NO: 2) corresponding to the two amino acids sequence was found by using TIGR unfinished *Streptococcus mutans* UAB159 DNA sequence database.

The obtained two DNA fragments encode the same protein with different sizes. The parent protein was secreted on a cell surface after biosynthesis and was partially digested by another proteinase. Namely, it was found that Lyt100 had signal sequence with 24 amino acids and the size of the mature form was 104.424 kDa. Partial digestion of the mature form protein removed amino-terminal 182 amino acids and resulted in 89.680 kDa.

Primers (SEQ ID NOs: 3, 4) were prepared based on DNA encoding the full-length protein and DNA encoding the mature form enzyme protein was amplified using *S. mutans*

C67-1 chromosome as a template. The DNA was inserted into an expression vector pQE30 and was transfected into *E. coli* M-15. One of the obtained transfomants was named as GY122.

(3) Purification of Recombinant Lytic Enzyme Lyt100

Figure 2:
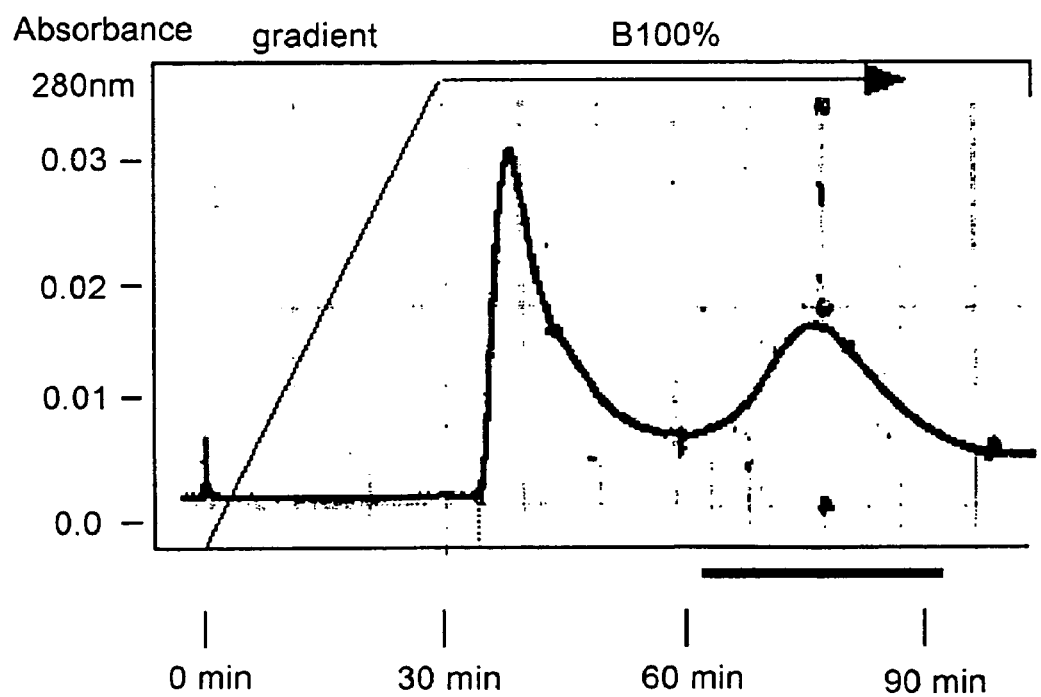
FIG. 2 is the column chromatogram of the enzyme Lyt100 of the present invention using TSKgek Phenyl-5PW. Underline shows the positions with lytic activity.

*E. coli* GY strain 122 was cultured in 500 ml of LB liquid medium (for about 4 hrs), was added final 1 mM isopropyl-D-thiogalactopyranocide when absorbance at 660 nm was 0.5. After further 3 hrs culture, the culture medium was centrifuged. After 30 min centrifugation at 8,300 g, the pellet was suspended in phosphate buffered-saline (PBS) (10 ml PBS for 1 g cell pellet), then the procedures of suspending and centrifugation were repeated for two times. The pellet finally obtained was suspended in phosphate buffered-saline (PBS) (10 ml PBS for 1 g cell pellet), was sonicated in ice-cold water (Tomy Seiko level 4, 50% interval, 20 min), and was centrifuged. The obtained pellet was suspended in PBS containing 0.2% Triton X-100 (10 ml PBS for 1 g pellet) and was left to stand at room temperature for 30 min. The above procedure was repeated again and the obtained pellet was dissolved in 8 to 10 volumes of 8 M urea, 0.1 M $Na_2PO_4$, 0.01 M Tris-HCl (pH 8.0). Ni-NTA resin beads (1 ml) was added to the obtained solution, was washed with 8 M urea, 0.1 M $Na_2PO_4$, 0.01 M Tris-HCl (pH 6.3) and was eluted by 8 M urea, 0.1 M $Na_2PO_4$, 0.01 M Tris-HCl (pH 5.4). Each fraction was 500 µl and the 15$^{th}$ to 20$^{th}$ fractions were collected. Each fraction was assayed for lytic activity, active fractions were collected and were dialyzed against 0.1 M phosphate buffer containing 1 M NaCl, 1 M urea at 4° C. for overnight. The dialysate was charged on a TSKgel Pheny-5PW (75 mm×7.5 mm, lot 5PHR0050) column of high performance liquid chromatography, which had been equilibrated with 0.1 M phosphate buffer (pH 7.0) containing 1 M NaCl and 1 M urea (A buffer). After washing with enough volume of the buffer, the A buffer was linearly changed to B buffer (0.1 M phosphate buffer, pH 7.0, containing 1 M urea) with a flow rate of 0.5 ml/min in 30 min to elute the active fraction. As shown in FIG. 2, the active fractions were eluted at the positions shown by a solid line.

Figure 3:
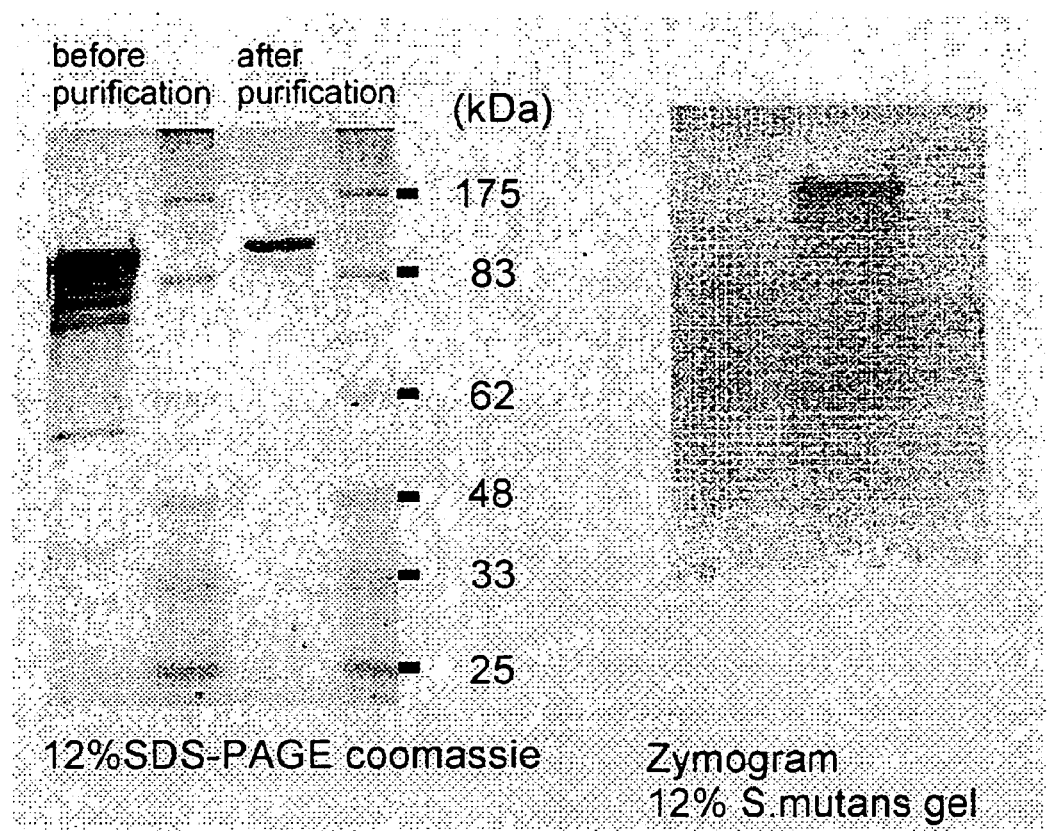
FIG. 3 is the electrophoresis profiles and the zymogram of the crude enzyme.

FIG. 3 shows SDS-gelelectrophoresis profiles for the sample before purification and after purification. The result that Lyt100 was electroporesed at the position of about 100 kDa (100±10 kDa) shows that the desired protein was purified.

Example 2

(4) Measurement of Lytic Activities Using Killed Cells

As oral streptococci, the following 5 strains were used: *S. mutans* C67-1, *S. sobrinus* OMZ176a, *S. mitis* ATCC9811, *S. sanguis* ATCC10436, and *S. salivarius* ATCC9222.

Heat killed bacterial cells in boiled water containing 4% SDS were washed with enough amount of water and were suspended in turbidity buffer (0.1 M phosphate buffer, 0.1 M NaCl, 1 mM Ca, pH 6.8) by adjusting absorbance to 0.3 at 660 nm. The purified Lyt100 was added to 2 ml cell suspension and the time course of the absorbance change was recorded.

Figure 4:
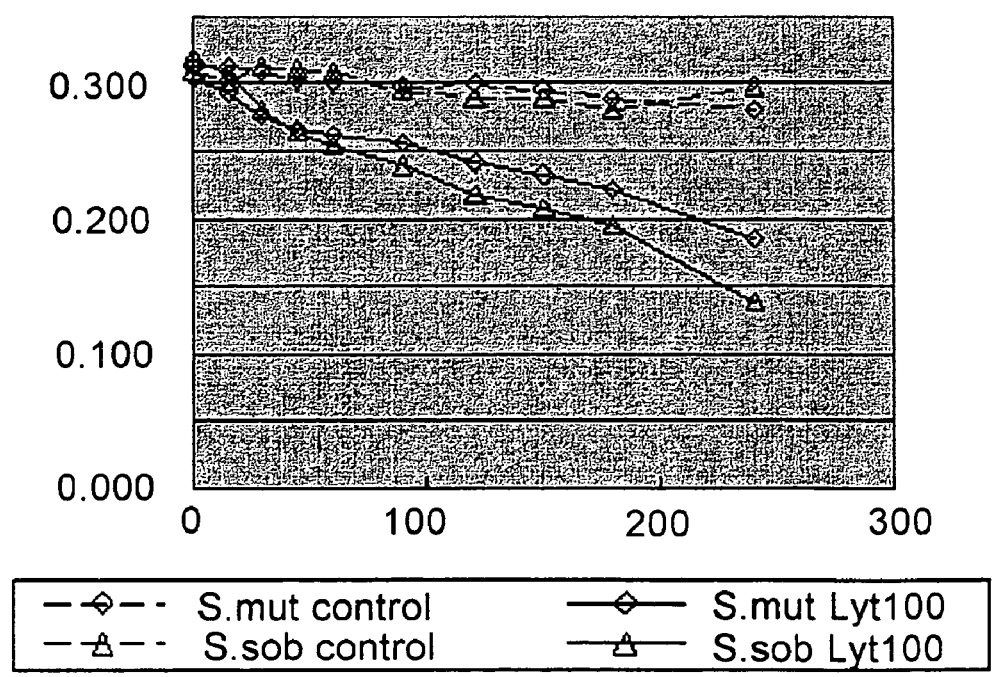
FIG. 4 is the lytic activity of the enzyme Lyt100 of the present invention against killed bacteria. The ordinate and horizontal axes show turbidity (generally, absorbance at 660 nm) and time (min.), respectively.
Figure 5:
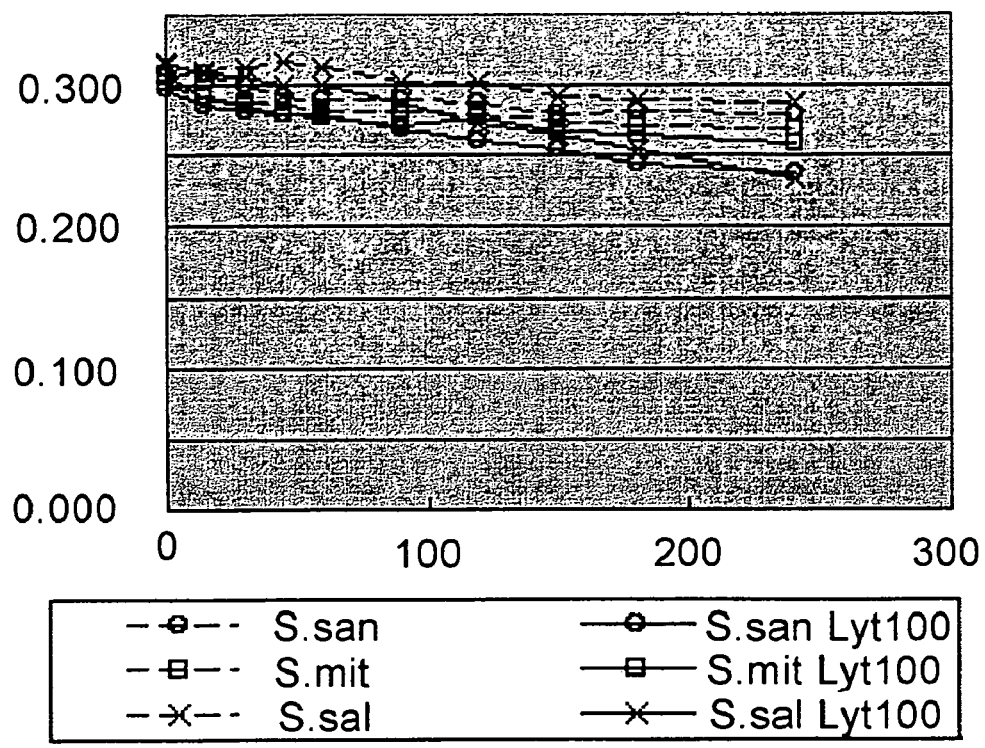
FIG. 5 is the lytic activity of the enzyme Lyt100 of the present invention against killed bacteria. The ordinate and horizontal axes show turbidity (generally, absorbance at 660 nm) and time (min.), respectively.
Figure 6:
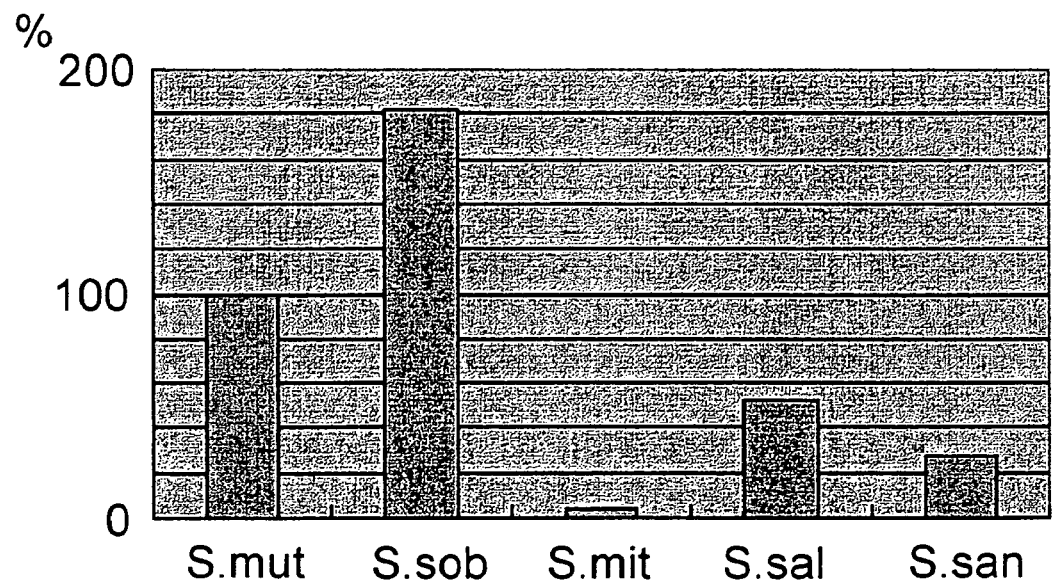
FIG. 6 is the lytic activity of the enzyme Lyt100 of the present invention against killed bacteria. Relative turbidity at 180 min to that using S. mutans as a substrate is shown by %.

The lytic activity against killed cells is shown in FIGS. 4 to 6. Lyt100 has strong lytic activity against *S. mutans* C67-1 and *S. sobrinus* OMZ176a, especially the activity against *S. sobrinus* OMZ176a was two times of that against *S. mutans*.

Example 3

(5) Measurement of Lytic and Bactericidal Activities Using Viable Bacteria

As oral streptococci, the following 5 strains were used: *S. mutans* C67-1, *S. sobrinus* OMZ176a, *S. mitis* ATCC9811, *S. sanguis* ATCC10436, and *S. salivarius* ATCC9222.

Cultured various strains of bacteria were suspended in turbidity buffer. In order to disperse the linkage of bacteria, *S. mutans* were sonicated at level 4 for 10 sec and other streptococci were sonicated at level 4 for 5 sec. Then, they were suspended in the buffer adjusting absorbance to 0.5 at 660 nm. Purified Lyt100 was added to 2 ml suspension and the time course of the change of absorbance was recorded. At the same time, the aliquots of the samples were diluted to $10^4$- to $10^5$-fold and were seeded on brain-heart-infusion agar media for *S. mutans* C67-1, *S. sobrinus* OMZ176a, *S. salivarius* ATCC9222 and on MS agar media for *S. mitis* ATCC9811, *S. sanguis* ATCC10436. Then viable number of colonies was counted.

Figure 7:
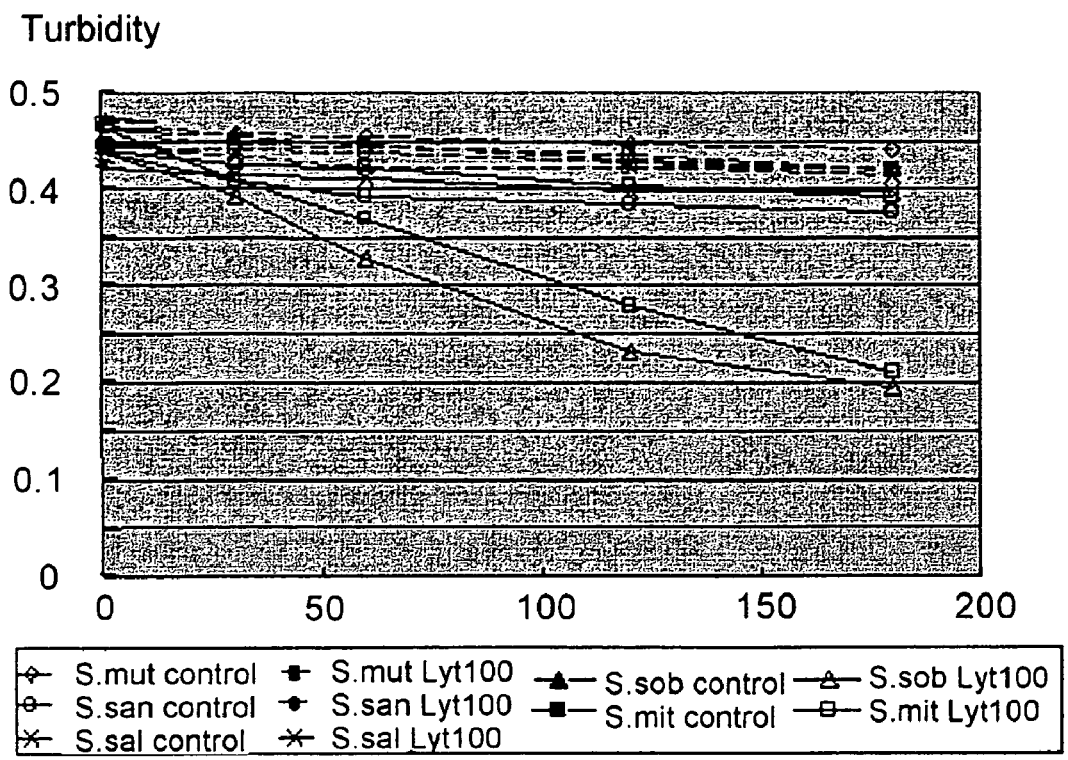
FIG. 7 is the lytic activity of the enzyme Lyt100 of the present invention against vaiable bacteria. The ordinate and horizontal axes show turbidity (generally, absorbance at 660 nm) and time (min.), respectively.
Figure 8:
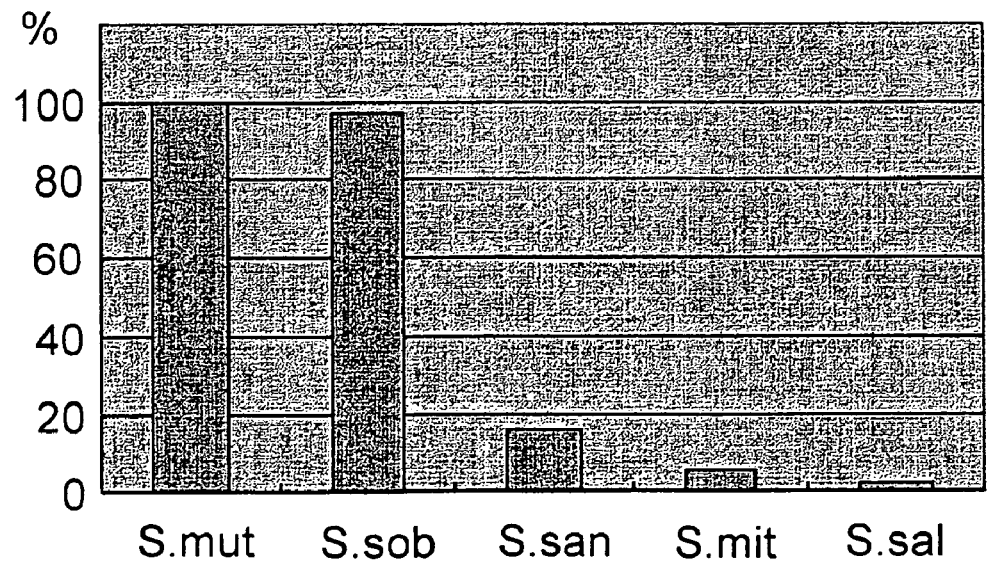
FIG. 8 is the lytic activity of the enzyme Lyt100 of the present invention against viable bacteria. Relative turbidity at 180 min to that using S. mutans as a substrate is shown by %.

FIGS. 7 and 8 show lytic activity against viable bacteria. Generally, viable bacteria are less sensitive against enzyme than killed bacteria. Lyt100 was used at 3 µg/2 ml in the lytic assay against killed bacteria, but at 10 µg/2 ml in that against viable bacteria. Even in the latter case, Lyt100 has strong lytic activity against *S. mutans* C67-1 and *S. sobrinus* OMZ176a.

Figure 9:
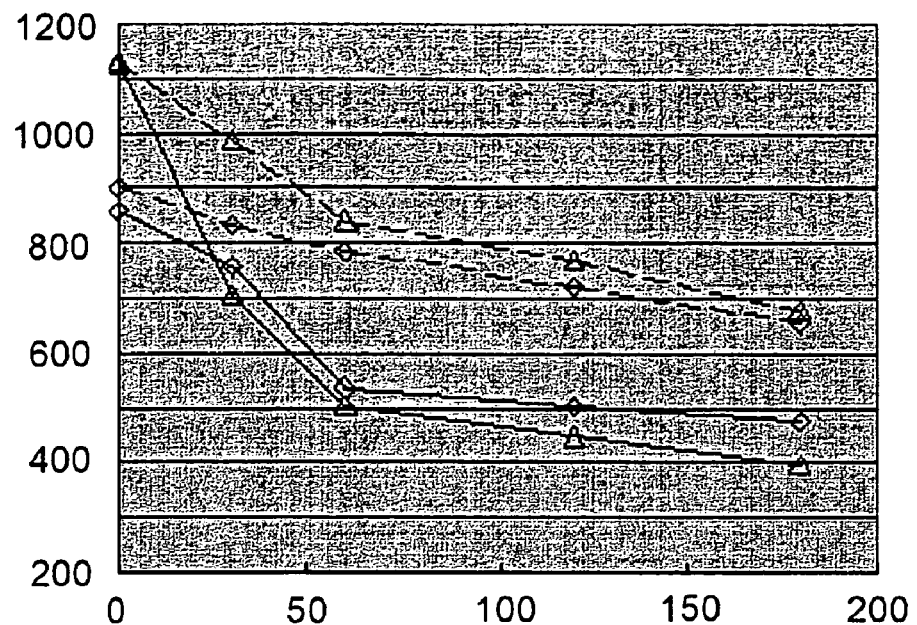
FIG. 9 is the bactericidal activity of the enzyme Lyt100 of the present invention against viable bacteria. The ordinate and horizontal axis show number of colonies (number of viable bacteria) and time (min.), respectively.
Figure 10:
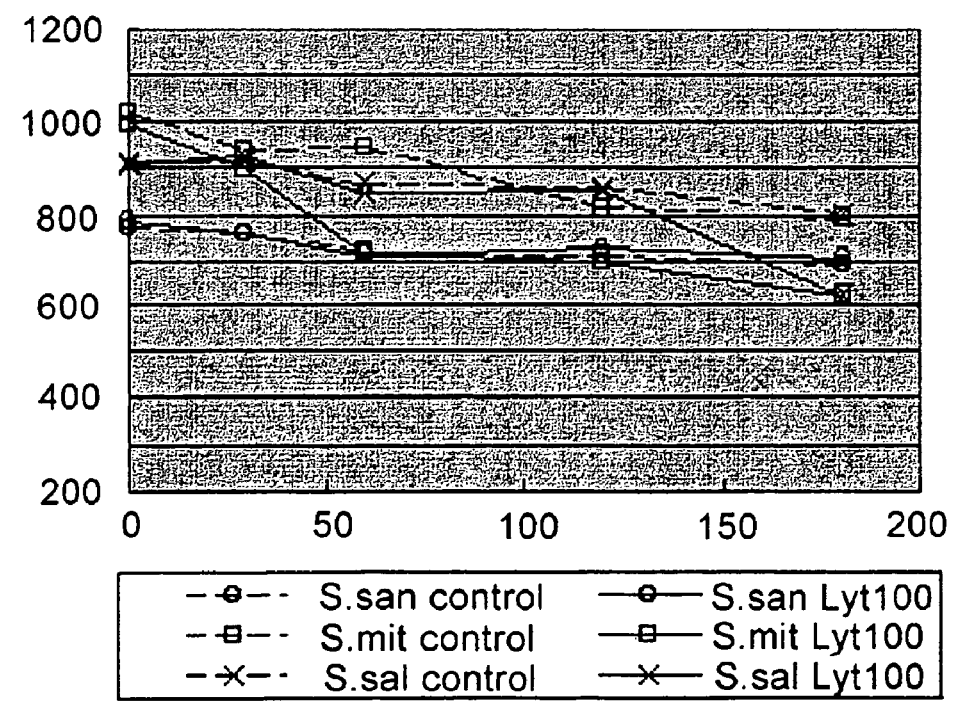
FIG. 10 is the bactericidal activity of the enzyme Lyt100 of the present invention against viable bacteria. The ordinate and horizontal axes show number of colonies (number of viable bacteria) and time (min.), respectively.

FIGS. 9 and 10 shows the bactericidal activity against viable bacteria. Colony forming unit was calculated for viable bacterial suspension treated with Lyt100 and the results were paralleled to that of turbidity decrease. It was found that Lyt100 had selective bactericidal effect against *S. mutans* C67-1 and *S. sobrinus* OMZ176a.

What is claimed is:

1. A bactericide against *Streptococcus mutans* and *Streptococcus sobrinus* comprising (1) or (2):
   (1) a protein comprising SEQ ID NO: 1; or
   (2) a protein comprising SEQ ID NO: 1, wherein the protein is obtained from cultured cells transformed by DNA comprising SEQ ID NO: 2 or DNA encoding SEQ ID NO: 1.

2. A composition for treating or preventing tooth decay comprising the bactericide of claim 1.

3. A method for selectively killing *Streptococcus mutans* and *Streptococcus sobrinus* by applying (1) or (2):
   (1) a protein comprising SEQ ID NO: 1; or
   (2) a protein comprising SEQ ID NO: 1, wherein the protein is obtained from cultured cells transformed by DNA comprising SEQ ID NO: 2 or DNA encoding SEQ ID NO: 1.

4. The composition of claim 2, wherein the composition is a toothpaste, an oral cavity cleaner, or a gum.

* * * * *